United States Patent [19]

Inoue et al.

[11] Patent Number: 4,468,340
[45] Date of Patent: Aug. 28, 1984

[54] LIQUID-CRYSTALLINE PHENYLCYCLOHEXANE DERIVATIVES

[75] Inventors: Hiromichi Inoue; Takashi Inukai; Yasuyuki Goto; Hideo Sato; Masahiro Fukui, all of Yokohamashi, Japan

[73] Assignee: Chisso Corporation, Osaka, Japan

[21] Appl. No.: 425,162

[22] Filed: Sep. 27, 1982

[30] Foreign Application Priority Data

Oct. 4, 1981 [JP] Japan .................................. 56-176698
Oct. 7, 1981 [JP] Japan .................................. 56-159593

[51] Int. Cl.$^3$ ........................ C09K 3/34; C07C 121/75
[52] U.S. Cl. ........................ 252/299.63; 260/465 F; 350/350 R
[58] Field of Search ............... 260/465 F; 252/299.63; 350/350 R

[56] References Cited

U.S. PATENT DOCUMENTS 4,130,502 12/1978 Eidenschink et al. ............. 252/299
4,154,697 5/1979 Eidenschink et al. ............. 252/299

OTHER PUBLICATIONS

"A Review of Some Liquid Crystal Materials and Their Properties", by G. W. Gray, (from Nov. 1977 3rd Symposium on Liquid Crystals), (Tokyo).

Primary Examiner—Dolph H. Torrence
Attorney, Agent, or Firm—Fred Philpitt

[57] ABSTRACT

New liquid-crystalline compounds having a positive dielectric anisotropy, trans-4-alkyloxymethyl-1-(4'-cyanophenyl)cyclohexanes and trans-4-alkyloxymethyl-1-(4''-cyano-4'-biphenylyl)cyclohexanes expressed by the general formula

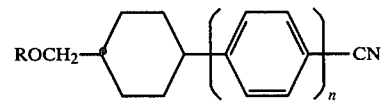

wherein R represents an alkyl group of 1 to 8 carbon atoms and n represents 1 or 2, are provided, which compounds are useful as a component constituting liquid-crystalline compositions having superior practical performances and being stable.

6 Claims, No Drawings

LIQUID-CRYSTALLINE PHENYLCYCLOHEXANE DERIVATIVES

BACKGROUND OF THE INVENTION

This invention relates to novel organic compounds. More particularly it relates to novel liquid-crystalline compounds having a positive dielectric anisotropy and being usable as a component of liquid-crystalline materials.

As well known, liquid-crystalline substances have been applied not only to display elements using nematic liquid crystals having a twisted liquid-crystalline arrangement (the so-called TN cell), but also widely to display elements utilizing the guest-host effect of liquid-crystalline substances or mixtures thereof containing a suitable dyestuff, further, DS type display elements utilizing the dynamic scattering effect of liquid crystals, display elements utilizing the transition of cholesteric-nematic phases, DAP type display elements utilizing the electric field-controlling birefringence effect of liquid crystals or the like display elements. As to these liquid-crystalline materials, it is the present status that none of single compounds can endure practical use with respect of vaious characteristic properties such as liquid-crystalline temperature range, actuation voltage, response performance, etc., but several liquid-crystalline compounds are blended together for practical use to obtain those which are endurable to practical use to a certain extent. The object of the present invention is to provide compounds useful as a component of liquid-crystalline compounds which have such superior practical performances and are stable.

SUMMARY OF THE INVENTION

The present invention resides mainly in: trans-4-alkyloxymethyl-1-(4'-cyanophenyl)cyclohexanes and trans-4-alkyloxymethyl-1-(4''-cyano-4'-biphenylyl)cyclohexanes expressed by the general formula

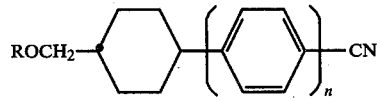

wherein R represents an alkyl group of 1 to 9 carbon atoms and n represents 1 or 2.

DETAILED DESCRIPTION OF THE INVENTION

The compounds of the present invention expressed by the formula (I) have a positive dielectric anisotropy, and when the compounds of the present invention are added to liquid crystals having a nearly zero or negative dielectric anisotropy, it is possible to obtain liquid-crystalline compositions having a positive anisotropy. Further, when the compounds are added to liquid crystals having a positive dielectric anisotropy, it is possible to reduce the threshold voltage of their electrooptical response.

The following compounds have already been known as compounds having a similar structure to those of the compounds of the present invention:

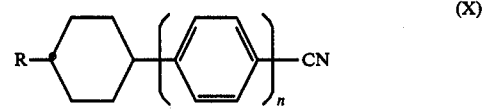

wherein R represents a straight chain alkyl group and n is 1 or 2.

When the compounds of the formula (X) are compared with those of the present invention (I), the refractive anisotropy i.e. $\Delta n$ of the former (X) is almost similar to that of the latter (I) and the viscosity of the former is somewhat inferior to that of the latter, but the dielectric anisotropy $\Delta \epsilon$ of the latter is much larger than that of the former as shown in the following Table:

| (I) | (X) (the chain length of molecule is similar to that of (I).) |
|---|---|
| CH$_3$OCH$_2$—⟨⟩—⟨⟩—CN, $\Delta\epsilon$ = 17.5 | C$_3$H$_7$—⟨⟩—⟨⟩—CN, $\Delta\epsilon$ = 11.6 |
| C$_3$H$_7$OCH$_2$—⟨⟩—⟨⟩—CN, $\Delta\epsilon$ = 13.0 | C$_5$H$_{11}$—⟨⟩—⟨⟩—CN, $\Delta\epsilon$ = 9.9 |
| C$_3$H$_7$OCH$_2$—⟨⟩—⟨⟩—⟨⟩—CN, $\Delta\epsilon$ = 12.3 | C$_5$H$_{11}$—⟨⟩—⟨⟩—⟨⟩—CN, $\Delta\epsilon$ = 9.3 |

Accordingly, when the compounds of the present invention are used as a component of liquid-crystalline compounds, it is possible to reduce the actuation voltage.

In addition, as other liquid-crystalline compounds having a large $\Delta\epsilon$, the following compounds are known:

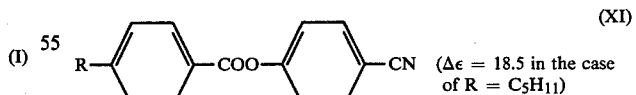

($\Delta\epsilon$ = 18.5 in the case of R = C$_5$H$_{11}$)

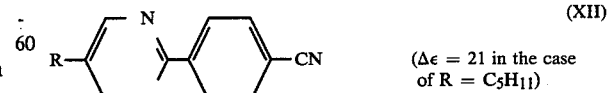

($\Delta\epsilon$ = 21 in the case of R = C$_5$H$_{11}$)

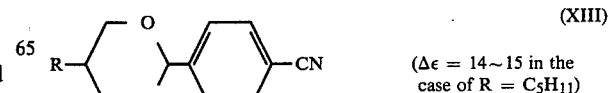

($\Delta\epsilon$ = 14~15 in the case of R = C$_5$H$_{11}$)

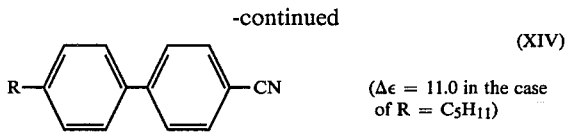

(Δε = 11.0 in the case of R = $C_5H_{11}$)

The compounds of (X1) and (X111) are higher in the viscosities than and inferior in the response speed to the compounds of the present invention.

Among the compounds of the present invention, the compounds ($I_a$) of n=1 in the formula (I) are very large in the value of Δε, and nevertheless relatively low in the viscosity; hence they are very useful as a liquid-crystalline material for low voltage drive. Further, the compounds ($I_b$) of n=2 in the formula (I) have higher N-I points; hence they are useful as a liquid crystal for broadening the liquid-crystalline temperature range of liquid-crystalline compositions, the so-called high temperature liquid crystal.

Further, the compounds of the present invention are liquid-crystalline compounds having a superior stability. Also, they are superior in the compatibility with other liquid-crystalline compounds. Thus when they are mixed with one kind of or a mixture of several kinds of liquid-crystalline compounds such as compounds of biphenyl group, ester group, azoxy group, cyclohexanecarboxylic acid phenyl ester group, phenylcyclohexane group, phenylpyrimidine group, phenylmetadioxane group, etc., it is possible to cause them to exhibit such effectiveness as elevation of N-I point, reduction in the drive voltage to change the response characteristics, etc., depending on the purposes of their uses.

The compounds of the formula (I) of the present invention can be synthesized through the following steps (A) (in the case of compounds of n=1 in the formula (I) i.e. those of the formula ($I_a$)):

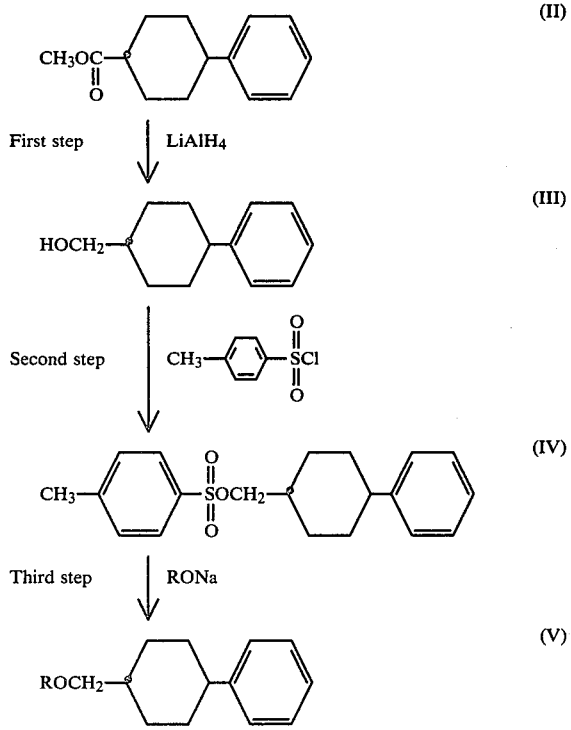

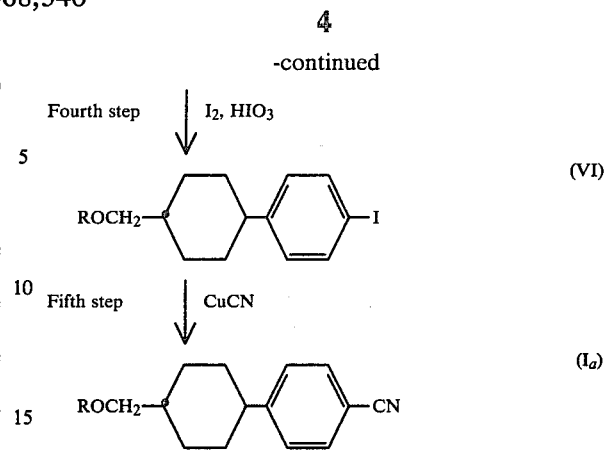

Firstly in the above steps, methyl trans-4-phenylcyclohexanecarboxylate (II) which is a known compound (see W. S. Johnson et al, J.A.C.S., 67, 1045 (1945)) is reduced with a reducing agent such as lithium-aluminum hydride ($LiAlH_4$) to obtain trans-4-phenylcyclohexylmethylalcohol (III), which is then reacted with p-toluenesulfonyl chloride in dry pyridine to obtain p-toluenesulfonic acid (trans-4-phenylcyclohexylmethyl) ester (IV). This compound (IV) is reacted with an alcoholate to obtain a trans-4-alkyloxymethyl-1-phenylcyclohexane (V), which is then heated together with iodine and iodic acid in a solvent to obtain a trans-4-alkyloxymethyl-1-(4'-iodophenyl)cyclohexane (VI), which is then reacted with a cyanogenating agent such as cuprous cyanide to obtain an objective compound of the formula ($I_a$).

When sodium methoxide, sodium ethoxide, sodium propoxide, sodium butoxide, sodium pentoxide, sodium hexyloxide, sodium heptyloxide or sodium octyloxide is used as a sodium alkoxide to be reacted with the compound (IV) in the third step, trans-4-methyloxymethyl-1-(4'-cyanophenyl)cyclohexane, trans-4-ethyloxymethyl-1-(4'-cyanophenyl)cyclohexane, trans-4-propyloxymethyl-1-(4'-cyanophenyl)cyclohexane, trans-4-butyloxymethyl-1-(4'-cyanophenyl)cyclohexane, trans-4-pentyloxymethyl-1-(4'-cyanophenyl)cyclohexane, trans-4-hexyloxymethyl-1-(4'-cyanophenyl)-cyclohexane, trans-4-heptyloxymethyl-1-(4'-cyanophenyl)-cyclohexane or trans-4-octyloxymethyl-1-(4'-cyanophenyl)cyclohexane, respectively, is obtained as the compounds of the formula ($I_a$) of the present invention which are final products.

Steps (B) in the case of compounds of n=2 in the formula (I)
i.e. Compounds of the formula ($I_b$)
The first step to the fourth step are all the same as those in the above steps (A). Thus the description of the steps (B) are started from the compound (IV) in the following scheme:

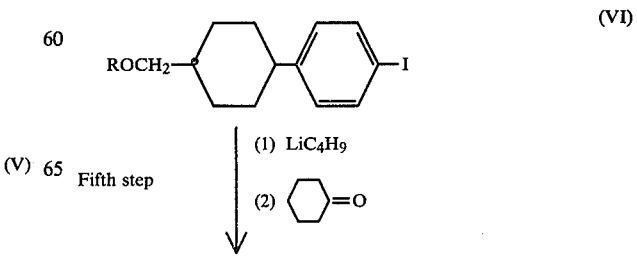

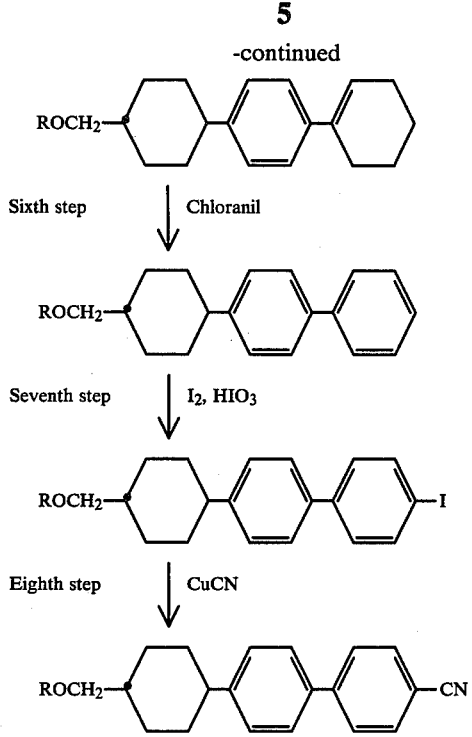

Sixth step — Chloranil

Seventh step — I₂, HIO₃

Eighth step — CuCN

In the above steps (B), firstly the iodine of the trans-4-alkyloxymethyl-1-(4'-iodophenyl)cyclohexane (VI) is substituted by lithium using a hexane solution of n-butyllithium, followed by reaction with cychohexanone to obtain a trans-4-alkyloxymethyl-1-(4'-cyclohexenyl-phenyl)cyclohexane (VII) (the fifth step), which is then heated together with a dehydrogenating agent such as chloranil, sulfur, etc. in a solvent to obtain a trans-4-alkyloxymethyl-1-(4'-biphenylyl)cyclohexane (VIII) (the sixth step). This compound (VIII) is heated together with iodine and iodic acid in a solvent to obtain a trans-4-alkyloxymethyl-1-(4''-iodo-4'-biphenylyl)cyclohexane (IX) (the seventh step), which is then reacted with a cyanogenating agent such as cuprous cyanide to obtain an objective compound of the formula (I$_b$) (the eighth step).

When sodium methoxide, sodium ethoxide, sodium propoxide, sodium butoxide, sodium pentoxide, sodium hexyloxide, sodium heptyloxide or sodium octyloxide is used as a sodium alkoxide to be reacted with the compound (IV) in the third step, trans-4-methyloxymethyl-1-(4'-cyanobiphenylyl)cyclohexane, trans-4-ethyloxymethyl-1-(4''-cyano-4'-biphenylyl)cyclohexane, trans-4-propyloxymethyl-1-(4''-cyano-4'-biphenylyl)cyclohexane, trans-4-butyloxymethyl-1-(4''-cyano-4'-biphenylyl)cyclohexane, trans-4-pentyloxymethyl-1-(4''-cyano-4'-biphenylyl)cyclohexane, trans-4-hexyloxymethyl-1-(4''-cyano-4'-biphenylyl)cyclohexane, trans-4-heptyloxymethyl-1-(4''-cyano-4'-biphenylyl)cyclohexane or trans-4-octyloxymethyl-1-(4''-cyano-4'-biphenylyl)cyclohexane, respectively, is obtained as compounds of the formula (I$_b$) of the present invention which are final products.

The compounds of the present invention will be further described in more detail by way of preparation examples and use examples thereof.

EXAMPLE 1

Preparation of trans-4-methyloxymethyl-1-(4'-cyanophenyl)cyclohexane

First step

Dried tetrahydrofuran (THF) (420 ml) was added to aluminum-lithium hydride (11.1 g, 0.293 mol) and the mixture was vigorously agitated. To the mixture was dropwise added a solution of methyl trans-4-phenylcyclohexanecarboxylate (II) (64.0 g, 0.293 mol) dissolved in THF (70 ml) while the reaction temperature was kept at 20° C. or lower. After completion of the dropwise addition, the mixture was warmed up to 55° C., reacted for 2 hours and cooled. Ethyl acetate (12 ml) and water (100 ml) were then added, followed by adding 18% sulfuric acid (350 ml) to give two separated layers: tetrahydrofuran layer and water layer. n-Heptane (200 ml) was added and the mixture was transferred into a separating funnel, followed by washing it with water (500 ml), washing with a 2% sodium carbonate aqueous solution (500 ml) and further washing with water till the aqueous layer becomes neutral. Heptane and THF were distilled off and the solid remaining in the distilation kessel was recrystallized from heptane (20 ml), and separated by filtration, followed by drying crystals to obtain 4-phenyl-cyclohexylmethylalcohol (III) (51.4 g) having a melting point of 47.3°~48.5° C.

Second step

The compound (III) (50 g, 0.268 mol) obtained in the first step was dissolved in dry pyridine (110 ml) and the solution was cooled to 5° C. or lower. To this solution was dropwise added a solution of p-toluenesulfonic acid chloride (50.1 g, 0.263 mol) dissolved in dry toluene (70 ml), in small portions through a dropping funnel so that the reaction temperature did not exceed 10° C. After completion of the dropwise addition, the cooling bath was removed and the reaction mixture was agitated at room temperature for 4 hours, followed by adding water (100 ml) and toluene (300 ml) and stirring. The mixture was transferred into a separating funnel and the toluene layer was washed twice with 6N-HCl aqueous solution (100 ml), then once with water (200 ml), further twice with 2N-NaOH aqueous solution (100 ml) and then four times with water (200 ml). Toluene was distilled off under reduced pressure and the resulting crystals were recrystallized from toluene (90 ml), followed by separating the crystals by filtration to obtain p-toluenesulfonic acid (trans-4-phenylcyclohexylmethyl) ester (IV) (77 g) having a melting point of 108.0°~108.7° C.

Third step

To methyl alcohol (250 ml) agitated at room temperature was added metallic sodium (17.4 g, 0.755 mol) finely sliced, in small portions to prepare sodium methoxide. After the metallic sodium slices disappeared, a solution of the compound (IV) (200 g, 0.581 mol) obtained in the second step, dissolved in dry toluene (600 ml) was gradually added through a dropping funnel so as to keep the inner temperature in the range of 50°~60° C. After completion of the dropwise addition, the mixture was subjected to reflux for 4 hours, followed by cooling, adding water (20 ml), transferring the mixture into a separating funnel, and washing the toluene layer with water till the aqueous layer became neutral. After distilling off toluene under reduced pressure, the residue was subjected to distillation under reduced pressure and fractions having boiling points of 105°~108° C./1.5 mmHg were collected to obtain trans-4-methyloxymethyl-1-phenylcyclohexane (V) (100.0 g).

Fourth step

Into a 1 l capacity three-neck flask were added the compound (V) (100.0 g, 0.490 mol) obtained in the third step, acetic acid (344 ml), water (91 ml), iodic acid (20.6 g, 0.117 mol), iodine (54.5 g, 0.215 mol), carbon tetrachloride (40 ml) and conc. sulfuric acid (14 ml). The mixture was agitated, heated by a mantle heater and subjected to reflux for 3 hours. After completion of the reaction, the reaction mixture was cooled to room temperature, followed by adding a 10% sodium thiosulfate aqueous solution (about 15 ml) to cause the color of excess iodine to disappear. n-Heptane (200 ml) was added and the mixture was transferred into a separating funnel, followed by washing it with water till the aqueous layer became neutral, distilling off n-heptane under reduced pressure, dissolving the residue in n-hexane (50 ml), allowing the solution to stand at −10° to −20° C. for 12 hours, separating the resulting crystals by filtration and drying them to obtain trans-4-methyloxymethyl-1-(4′-iodophenyl)cyclohexane (VI) (81.8 g) having a melting point of 40.3°∼42.3° C.

Fifth step

In a 300 ml three-neck flask, N,N-dimethylformamide (DMF) (63 ml) was added to the compound (VI) (20 g, 0.061 mol) obtained in the fourth step and cuprous cyanide (6.3 g, 0.071 mol). The mixture was agitated, heated by a mantle heater and subjected to reflux for 6 hours. After completion of the reaction, the reaction liquid was cooled to room temperature, followed by adding a 28% ammonia aqueous solution (18 ml), agitating, adding heptane (50 ml) for extraction, removing insoluble matters in the heptane layer by suction filtration, transferring the filtrate to a separating funnel, washing the heptane layer with 6N-HCl (50 ml), further washing with 2N-NaOH aqueous solution (50 ml) and washing with water till the aqueous layer became neutral. The resulting heptane layer was dried with anhydrous sodium sulfate (10 g) and then passed through an activated alumina layer filled in a column. The heptane solution passing through the activated alumina layer was concentrated under reduced pressure, and the resulting raw crystals were recrystallized from ethanol (10 ml), followed by filtering off and drying to obtain the objective trans-4-methyloxymethyl-1-(4′-cyanophenyl)cyclohexane (I) (6.4 g). This product had a melting point (C-I point) of 59.9° C. Further this product was mixed with trans-4-pentyl-1-(4′-cyanophenyl)cyclohexane and the melting point of the mixture was measured. By extrapolating the resulting value, it was found that the product had a N-I point of 29.1° C. The elemental analysis values of the product accorded well with its calculated values as follows:

|   | Observed values (%) | Calculated values (%) (as C$_{15}$H$_{19}$NO) |
| --- | --- | --- |
| C | 78.5 | 78.57 |
| H | 8.3 | 8.35 |
| N | 6.0 | 6.10 |

EXAMPLE 2

The following compounds were synthesized in the same manner as in Example 1 except that methyl alcohol in the third step of Example 1 was replaced by ethyl alcohol or propyl alcohol:

Trans-4-ethyloxymethyl-1-(4′-cyanophenyl)cyclohexane (m.p., 44.0°∼44.5° C., N-I point, −2.4° C.).

Trans-4-propyloxymethyl-1-(4′-cyanophenyl)cyclohexane (m.p., 24.5° C.; N-I point, −13.9° C.).

EXAMPLE 3

Preparation of trans-4-methyloxymethyl-1-(4″-cyano-4′-biphenylyl)cyclohexane

The first step to the fourth step in the preparation of this compound are the same as those in Example 1.

Fifth step

Into a 500 ml three-neck flask were fed the compound (VI) (30 g, 0.091 mol) obtained in the fourth step of Example 1 and dry toluene (60 ml) in a dry nitrogen atmosphere and the compound was dissolved in toluene with stirring at 20° C. To the solution was dropwise added a hexane solution (68.9 ml) of 1.67 N n-butyllithium (0.921 mol) over about 10 minutes while the liquid temperature was kept at 20° to 25° C. After completion of the dropwise addition, the mixture was kept at 25° C. for 30 minutes and then cooled to 5° C., followed by dropwise adding cyclohexanone (10.3 g, 0.105 mol) over 20 minutes while the mixture was kept at 5° to 10° C. After the addition, the mixture was kept at 45° C. for 30 minutes, followed by dropwise adding water (30 ml) and further dropwise adding 6N hydrochloric acid (60 ml) while the mixture was kept at 30° C. or lower. The resulting liquid was separated into a lower aqueous layer and an upper organic layer. The lower layer was discarded. Potassium hydrogen sulfate (KHSO$_4$) (3 g) was added to the upper layer and the mixture was heated for distilling off the solvent, followed by concentrating the resulting liquid till the liquid temperature reached 110° C.; during this concentration, dehydration reaction advanced. After the reaction, the reaction liquid was cooled and transferred into a separating funnel, followed by twice washing with water, distilling off the solvent and recrystallizing the residue from ethyl alcohol (10 ml) to obtain purified trans-4-methyloxymethyl-1-(4′-cyclohexenylphenyl)cyclohexane (VII) (7.8 g) having a melting point of 74.8°∼75.5° C.

Sixth step

Into a 300 ml three-neck flask were introduced the compound (VII) (7.8 g, 0.027 mol) obtained in the fifth step, chloranil (15.5 g, 0.063 mol) and xylene (130 ml), and they were subjected to reflux on heating. After cooling, insoluble solid was removed by filtering off, and toluene was removed by concentration, followed by recrystallizing the resulting raw crystals from ethyl alcohol (5 ml) to obtain trans-4-methyloxymethyl-1-(4′-biphenylyl)cyclohexane (VIII) (2.9 g) having a melting point of 67.3°∼69.5° C.

Seventh step

Into a 100 ml three-neck flask were added the compound (VIII) (2.9 g, 0.011 mol) obtained in the sixth step, acetic acid (8 ml), water (2 ml), iodic acid (0.44 g, 0.002 mol), iodine (1.2 g, 0.004 mol), carbon tetrachloride (1 ml) and conc. sulfuric acid (0.8 ml), and they were subjected to reflux for 3 hours on heating. After completion of the reaction, a 10% sodium thiosulfate aqueous solution (about 2 ml) was added while the reaction liquid was still hot, to cause the color of excess iodine to disappear. The liquid was cooled and the resulting crystals were separated by filtering and recrystallized from ethyl acetate (10 c.c.) to obtain trans-4-methyloxymethyl-1-(4″-iodo-4′-biphenylyl)cyclohexane (IX) (2.8 g). This product was also a liquid crystal and had a melting point (C-N point) of 156.2° C. and a transparent point (N-I point) of 158.0° C.

Eighth step

Into a 100 ml three-neck flask were added the compound (IX) (2.8 g, 0.007 mol) obtained in the seventh step, cuprous cyanide (0.72 g, 0.008 mol) and N,N-dimethylformamide (DMF) (15 ml), and they were heated with stirring under reflux for 6 hours, followed by cooling, adding an aqueous ammonia (28%) (2.2 ml) and further adding toluene (30 ml). From the resulting liquid was separated on organic layer which was then washed with a dilute hydrochloric acid, then with a dilute sodium hydroxide aqueous solution and further with water, followed by removing a small amount of solid matters by filtering, distilling off the solvent under reduced pressure, dissolving the residue in dry toluene (50 ml), passing the solution through a column chromatogram layer filled with alumina and concentrating the toluene layer to obtain an objective purified compound, trans-4-methyloxymethyl-1-(4″-cyano-4′-biphenylyl)cyclohexane (I) (1.1 g) having a melting point (C-N point) of 156.7° C. and a transparent point (N-I point) of 226.8° C. Its elemental analysis values accorded well with its calculated values as follows:

|   | Observed values (%) | Calculated values (%) (as $C_{21}H_{23}NO$) |
|---|---|---|
| C | 82.5 | 82.59 |
| H | 7.5  | 7.59  |
| N | 4.5  | 4.58  |

EXAMPLE 4

The following compounds were obtained in the same manner as in Example 3 except that methyl alcohol of the third step in Example 3 was replaced by ethyl alcohol, propyl alcohol or pentyl alcohol:

Trans-4-ethyloxymethyl-1-(4″-cyano-4′-biphenylyl)-cyclohexane (C-N point, 106.6° C.; N-I point, 194.4° C.)

Trans-4-propyloxymethyl-1-(4″-cyano-4′-biphenylyl)cyclohexane (C-N point, 92.2° C.; N-I point, 180.0° C.)

Trans-4-pentyloxymethyl-1-(4″-cyano-4′-biphenylyl)cyclohexane (C-N point, 89.8° C.; N-I point, 171.2° C.).

EXAMPLE 5 (USE EXAMPLE 1)

A liquid-crystalline composition consisting of

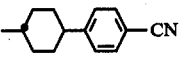  19.2 parts by weight

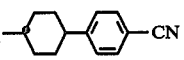  28.8 parts by weight

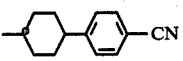  20.0 parts by weight and

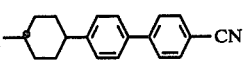  12.0 parts by weight, has a nematic liquid-crystalline temperature range of $-10°$ to $+72.3°$ C., a viscosity at 20° C., $\eta_{20}$ of 29 cp and a dielectric anisotropy $\Delta\epsilon$ of 11.5 ($\epsilon_{\parallel}=15.9$, $\epsilon_{\perp}=4.4$). When this composition was sealed in a TN cell of 10 μm thick, the resulting threshold voltage and saturation voltage were 1.69 V and 2.37 V, respectively.

When

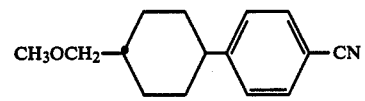

which is one of the compounds of the present invention, in an amount of 20 parts by weight, was added to the above composition, the resulting liquid-crystalline composition had a nematic liquid-crystalline temperature range of $-15°$ to $+62.5°$ C., a $\eta_{20}$ of 30 cp and a $\Delta\epsilon$ of 12.7 ($\epsilon_{\parallel}=18.1$, $\epsilon_{\perp}=5.4$), and when the composition was sealed in the same cell as the above-mentioned, the resulting threshold voltage and saturation voltage were 1.39 V and 2.02 V, respectively, that is, the both were reduced.

EXAMPLE 6 (USE EXAMPLE 2)

A liquid-crystalline composition consisting of

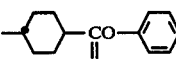  10 parts by weight

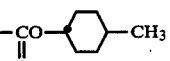  10 parts by weight

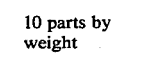  20 parts by weight

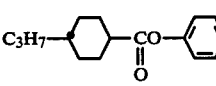  20 parts by weight, and

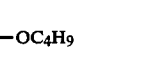  20 parts by weight, has a nematic liquid-crystalline temperature range of $-10°$ to $+70.3°$ C., a viscosity at 20° C., $\eta_{20}$ of 27.6 cp and a dielectric anisotropy $\Delta\epsilon$ of $-0.9$ ($\epsilon_{\parallel}=3.7$, $\epsilon_{\perp}=4.6$). When this composition was sealed in a TN cell of 10 μm thick, normal actuation was impossible since its $\Delta\epsilon$ value is negative.

To this composition were added

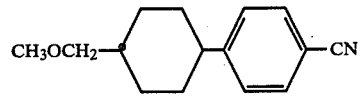

(10 parts by weight),

[Structure: C2H5OCH2-cyclohexyl-phenyl-CN]

(5 parts by weight) and

[Structure: C6H11OCH2-cyclohexyl-phenyl-CN]

(5 parts by weight) which all are the compounds of the present invention, and the resulting liquid-crystalline composition had a nematic liquid-crystalline temperature range of $-20°$ to $+60.2°$ C., a $\eta_{20}$ of 31 cp and a $\Delta\epsilon$ of 3.6 ($\epsilon_\parallel = 9.2$, $\epsilon_\perp = 5.6$). When this composition was sealed in the same cell as the above-mentioned, the threshold voltage and saturation voltage were 1.71 V and 2.31 V, respectively.

EXAMPLE 7 (USE EXAMPLE 3)

A liquid-crystalline composition consisting of

[Structure: C3H7-cyclohexyl-phenyl-CN]  27.27 parts by weight

[Structure: C5H11-cyclohexyl-phenyl-CN]  36.36 parts by weight, and

[Structure: C7H15-cyclohexyl-phenyl-CN]  27.27 parts by weight has a nematic liquid-crystalline temperature range of $-3°$ to $+52.5°$ C., a viscosity at 20° C., $\eta_{20}$ of 23 cp and a dielectric anisotropy $\Delta\epsilon$ of 11.3 ($\epsilon_\parallel = 16.2$ and $\epsilon_\perp = 4.9$). When the composition was sealed in a TN cell of 10 μm thick, the resulting threshold voltage and saturation voltage were 1.5 V and 2.2 V, respectively.

When

[Structure: C3H7OCH2-cyclohexyl-phenyl-phenyl-CN]

(ten parts by weight) of Example 4 which is one of the compounds of the present invention was added to the above liquid-crystalline composition, the resulting liquid-crystalline composition had a nematic liquid-crystalline temperature range of $-4°$ to $+60.1°$ C. (that is, the range was broadened mainly toward higher temperatures), a $\eta_{20}$ of 28.2 cp and a $\Delta\epsilon$ of 11.4 ($\epsilon_\parallel = 16.1$, $\epsilon_\perp = 4.7$), and when this composition was sealed in the same TN cell as the above-mentioned, the resulting threshold voltage and saturation voltage were 1.6 V and 2.3 V, respectively.

EXAMPLE 8 (USE EXAMPLE 4)

A liquid-crystalline composition consisting of

[Structure: C3H7-cyclohexyl-COO-phenyl-OC4H9]  21.25 parts by weight

[Structure: C4G9-cyclohexyl-COO-phenyl-OC2H5]  21.25 parts by weight

[Structure: C5H11-cyclohexyl-COO-phenyl-OCH3]  21.25 parts by weight, and

[Structure: CH3O-cyclohexyl-COO-phenyl-C5H11]  21.25 parts by weight has a nematic liquid-crystalline temperature range (MR) of $-9.6°$ to $+62.5°$ C., a viscosity at 20° C., $\eta_{20}$ of 27.6 cp and a dielectric anisotropy $\Delta\epsilon$ of $-0.9$ ($\epsilon_\parallel = 3.7$, $\epsilon_\perp = 4.6$). When this composition was sealed in a TN cell of 10 μm thick, normal actuation as TN cell was impossible since its $\Delta\epsilon$ value was negative.

When

[Structure: C2H5OCH2-cyclohexyl-phenyl-phenyl-CN]

(5 parts by weight,

[Structure: C3H7OCH2-cyclohexyl-phenyl-phenyl-CN]

(5 parts by weight) and

[Structure: C5H11OCH2-cyclohexyl-phenyl-phenyl-CN]

(5 parts by weight) which all are the compounds of the present invention, were added to the above liquid-crystalline composition, the resulting liquid-crystalline composition had a MR of $-8.4°$ to $+74.0°$ C. (that is, the range was broadened toward higher temperatures), a $\eta_{20}$ of 31 cp and a $\Delta\epsilon$ of 2.2 ($\epsilon_\parallel = 7.1$, $\epsilon_\perp = 4.9$). When this composition was sealed in the same TN cell as the above-mentioned, the resulting threshold voltage and saturation voltage were 2.9 V and 3.9 V, respectively, and the TN cell was normally actuated.

What is claimed is:

1. Trans-4-alkyloxymethyl-1-(4'-cyanophenyl)cyclohexanes and trans-4-alkyloxymethyl-1-(4''-cyano-4'-biphenylyl)cyclohexanes expressed by the general formula

[Structure: ROCH2-cyclohexyl-(phenyl)n-CN]   (I)

wherein R represents an alkyl group of 1 to 8 carbon atoms and n represents 1 or 2.

2. A process for producing trans-4-alkyloxymethyl-1-(4'-cyanophenyl)cyclohexanes of claim 1, which comprises the steps of
iodinating a trans-4-alkyloxymethyl-1-phenylcyclohexane wherein the alkyl group has 1 to 8 carbon atoms to obtain a trans-4-alkyloxymethyl-1-(4'-iodophenyl)cyclohexane, and then cyanogenating this trans-4-alkyloxymethyl-1-(4'-iodophenyl)cyclohexane with cuprous cyanide to obtain a trans-4-alkyloxymethyl-1-(4'-cyanophenyl)cyclohexane.

3. A process for producing trans-4-alkyloxymethyl-1-(4''-cyano-4'-biphenylyl)cyclohexanes of claim 1 which comprises the steps of
iodinating a trans-4-alkyloxymethyl-1-(4'-biphenylyl)cyclohexane to obtain a trans-4-alkyloxymethyl-1-(4''-iodo-4'-biphenylyl)cyclohexane, and then cyanogenating this trans-4-alkyloxymethyl-1-(4''-iodo-4'-biphenylyl)cyclohexane with cuprous cyanide to obtain a trans-4-alkyloxymethyl-1-(4''-cyano-4'-biphenylyl)cyclohexane.

4. Compounds of claim 1 expressed by the general formula

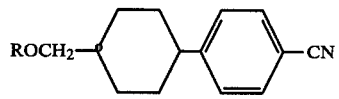

wherein R represents $CH_3$ or $C_2H_5$.

5. A liquid crystalline dielectric composition having at least 2 components, one of which is selected from the compounds set forth in claim 1.

6. A liquid crystalline display element whose dielectric comprises a compound set forth in claim 1.